United States Patent [19]

Canavan

[11] Patent Number: 5,530,490
[45] Date of Patent: Jun. 25, 1996

[54] SAFETY EYEGLASSES AND CORRECTIVE LENS CARRIER THEREFOR

[75] Inventor: Richard W. Canavan, East Woodstock, Conn.

[73] Assignee: Uvex Safety, Inc., Smithfield, R.I.

[21] Appl. No.: 190,865

[22] Filed: Feb. 1, 1994

[51] Int. Cl.⁶ .............................. G02C 1/00; G02C 5/14
[52] U.S. Cl. .................... 351/41; 351/106; 351/118; 351/120
[58] Field of Search ................... 351/44, 47, 57, 351/118, 125, 154, 158, 83, 120, 124, 116, 115; 2/10, 13, 441, 443, 449, 426

[56] References Cited

U.S. PATENT DOCUMENTS

| | | |
|---|---|---|
| 3,233,249 | 2/1966 | Baratelli et al. ........................ 351/44 |
| 3,395,406 | 8/1968 | Smith ....................................... 351/154 |
| 5,146,623 | 9/1992 | Paysan et al. ............................ 351/44 |
| 5,357,292 | 10/1994 | Wiedner .................................. 351/115 |

FOREIGN PATENT DOCUMENTS 2688322  9/1993  France ......................... 2/426

*Primary Examiner*—William L. Sikes
*Assistant Examiner*—Hung Xuan Dang
*Attorney, Agent, or Firm*—Salter & Michaelson

[57] ABSTRACT

A safety eyeglass assembly includes a carrier integrally molded from a transparent plastic material and including a front panel portion having a pair of lens apertures therein and left and right top, bottom and side shield extending rearwardly from left and right side portions of the front panel portion. The assembly further includes a frame detachably and adjustably secured to the carrier and including left and right temple frame portions and a cross bar portion extending between the temple frame portions in front of the carrier.

12 Claims, 3 Drawing Sheets

SAFETY EYEGLASSES AND CORRECTIVE LENS CARRIER THEREFOR

BACKGROUND AND SUMMARY OF THE INVENTION

The instant invention relates to protective eyewear and more particularly to a safety eyeglass assembly and to a carrier therefor which is adapted for use with corrective lenses.

The importance of wearing safety glasses in many industrial environments is widely recognized, and as a result, a variety of different types of safety eyeglasses have been heretofore available. However, only a relatively small number of the heretofore available safety eyeglasses have been adapted to incorporate corrective lenses, and therefore, it has frequently been common practice for wearers of safety eyeglasses, who also require corrective eyeglasses, to use relatively large cumbersome safety eyewear which can be worn over conventional corrective eyeglasses. However, this practice has been found to be unsatisfactory because it requires users to wear cumbersome, uncomfortable safety eyewear, and also because it requires users to look through two sets of lenses, i.e. both corrective lenses and safety lenses or shields. In order to overcome the problem of requiring users to wear bulky and cumbersome safety eyewear in addition to corrective eyewear, several manufacturers have produced safety eyewear which are adapted for mounting corrective lenses behind the safety lenses or shields thereof. However, eyewear of this type have also required users to look through two sets of lenses. Still further, while safety eyeglass frames have been heretofore available which have been adapted for receiving corrective lenses so that users only have to look through the corrective lenses, these safety eyeglass frames have generally been embodied as modified versions of conventional eyewear which, in many instances, have not provided adequate safety protection. Further, for the most part, eyeglass frames of this type have been found to lack versatility, and they have not provided users with the option of changing frame colors, etc.

The instant invention provides a novel and effective safety eyeglass assembly which is adapted for use with corrective lenses and which has a high degree of versatility. Specifically, the assembly of the instant invention comprises a carrier which is adapted for receiving corrective lenses therein and a frame which is adapted to be detachably and adjustably secured to the carrier. The carrier is adapted for receiving corrective lenses therein so that during use a user is only required to look through the corrective lenses and not through an additional lens or safety shield. Further, the carrier is adapted to be releasibly secured to the frame so that a user can interchange the frame for another frame of the same type, but of a different color or appearance.

Still more specifically, the safety eyeglass assembly of the instant invention comprises a carrier which is integrally molded from a clear transparent plastic material and which includes a front panel portion having a nose receiving portion and left and right lens receiving apertures therein which are adapted for snap-receiving corrective lenses. Specifically, the carrier is formed so that the peripheries of the lens apertures have V-shaped lens receiving grooves therein having enlarged posterior lips which allow lenses to be snap received therein from the front side of the carrier, but which prevent lenses from being disengaged therefrom in a rearward direction. The carrier further comprises left and right side shields extending rearwardly from left and right side extremities of the front panel portion, and left and right upper shields extending between left and right upper extremity portions of the front panel portion, and the left and right side shields, respectively. The carrier further comprises left and right lower shields extending between left and right lower extremity portions of the front panel portion and the left and right side shields, respectively. Accordingly, the carrier provides a clear transparent unit which is adapted for snap-receiving lenses therein and for effectively protecting the eyes of a wearer.

The eyeglass assembly further comprises a frame portion which is detachably and adjustably secured to the carrier, and which includes left and right temple frame portion and a cross bar portion extending between the temple frame portions in front of the carrier. The cross bar portion includes a front bar portion which extends in front of the front panel portion of the carrier and left and right side bar portions which extend along the left and right side shields, respectively, of the carrier. The front bar portion is preferably secured to the front panel portion of the carrier at a center pivot point, and the left and right side bar portions are preferably detachably secured to the left and right side shields, respectively, such that the left and right side bar portions are vertically adjustable relative to the left and right side shields, respectively, for adjusting the angular orientation of the frame relative to the carrier. The front panel portion of the carrier preferably includes a main front plate portion having left and right lens apertures therein and left and right rearwardly recessed upper portions above the left and right lens apertures, respectively. The front bar portion passes along the rearwardly recessed portions and it is, therefore, recessed at least partially rearwardly from the main front panel portion along the opposite upper side portions of the front panel portion. As a result, the main front plate portion can be constructed in a somewhat flatter configuration so as to position corrective lenses received in the left and right lens apertures more directly in front of the eyes of a user resulting in a reduction of the angle of the corrective lenses to the eyes of the user. Further, the left and right upper shields preferably extend rearwardly from the left and right rearwardly recessed portions, respectively, and the temple frame portions are preferably telescopically adjustable to different lengths.

It has been found that safety eyeglass assembly of the instant invention has significant advantages over the heretofore available safety eyeglasses. Specifically, because the carrier is integrally molded from a clear transparent plastic material and adapted for snap receiving corrective lenses therein, the eyeglass assembly of the subject invention provides clear, unobstructed viewing through a single set of lenses. Further, because the carrier is removable from the frame, the frame can be interchanged with another frame of a different color or appearance by simply disassembling the carrier with the lenses therein from the original frame and assembling it with a new frame. Still further, because of the unitized construction of the carrier and the manner in which it is adapted for snap receiving corrective lenses therein, the carrier with the lenses received therein provides highly effective eye protection. Still further, the overall construction of the carrier enables the safety eyeglasses of the subject invention to be comfortably and effectively worn by a user for a prolonged period of time.

Accordingly, it is a primary object of the instant invention to provide an effective safety eyeglass assembly which is adapted for use with corrective lenses.

Another object of the instant invention is to provide a safety eyeglass assembly comprising a removable carrier which is adapted for snap receiving corrective lenses therein.

An even still further object of the instant invention is to provide a safety eyeglass assembly comprising a carrier which is adapted for receiving corrective lenses therein and a frame which is detachable from the carrier for interchanging the frame with another frame of a different color or appearance.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

DESCRIPTION OF THE INVENTION

Figure 1:
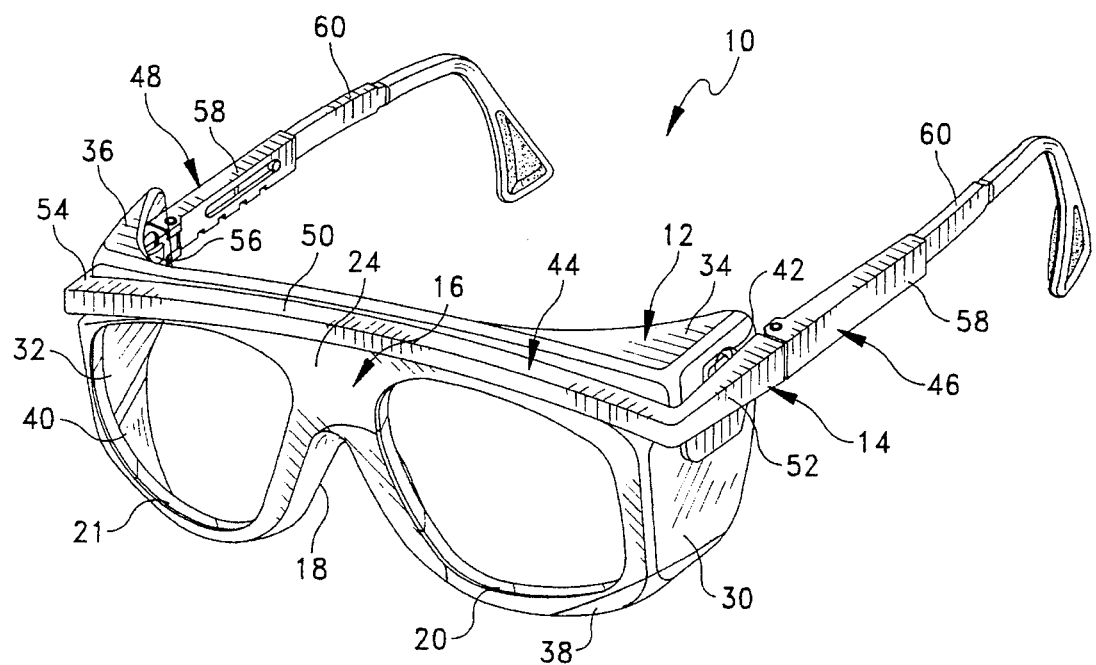
FIG. 1 is a perspective view of the eyeglass assembly of the instant invention.
Figure 2:
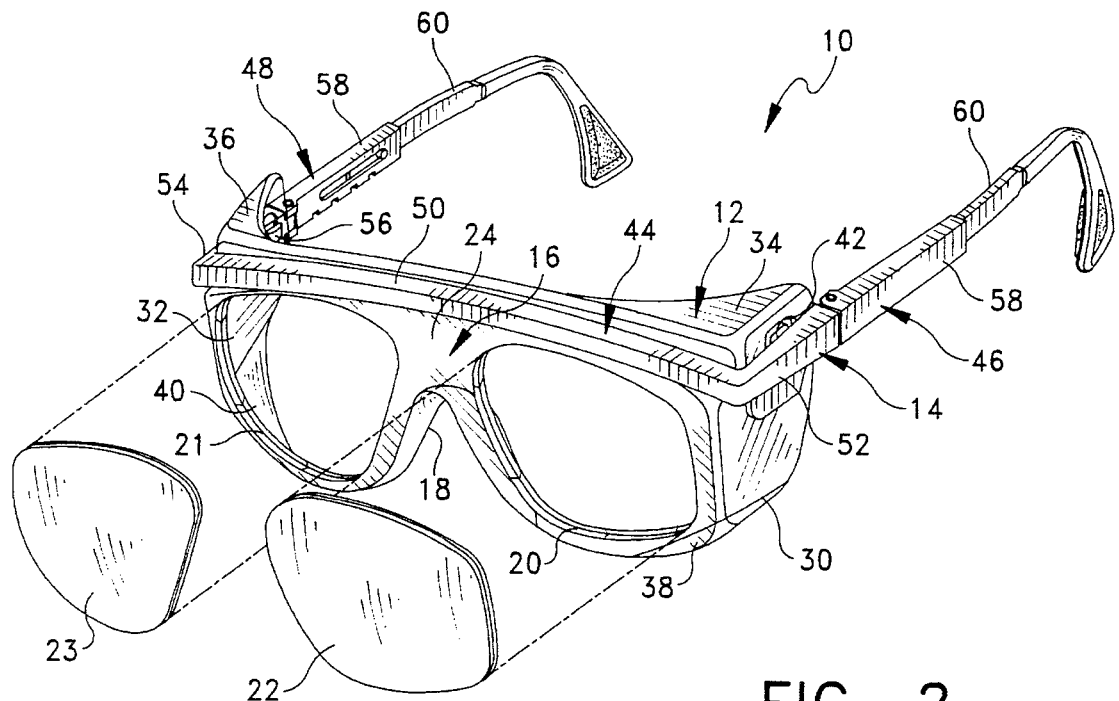
FIG. 2 is a perspective view thereof with a pair of corrective lenses in exploded relation.
Figure 3:
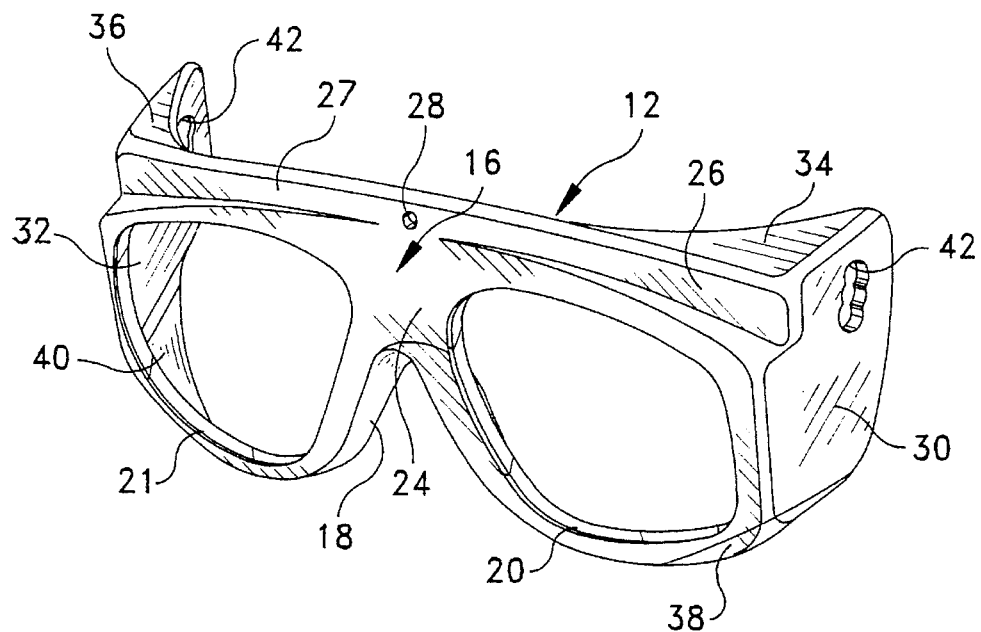
FIG. 3 is a perspective view of the carrier per se.
Figure 4:
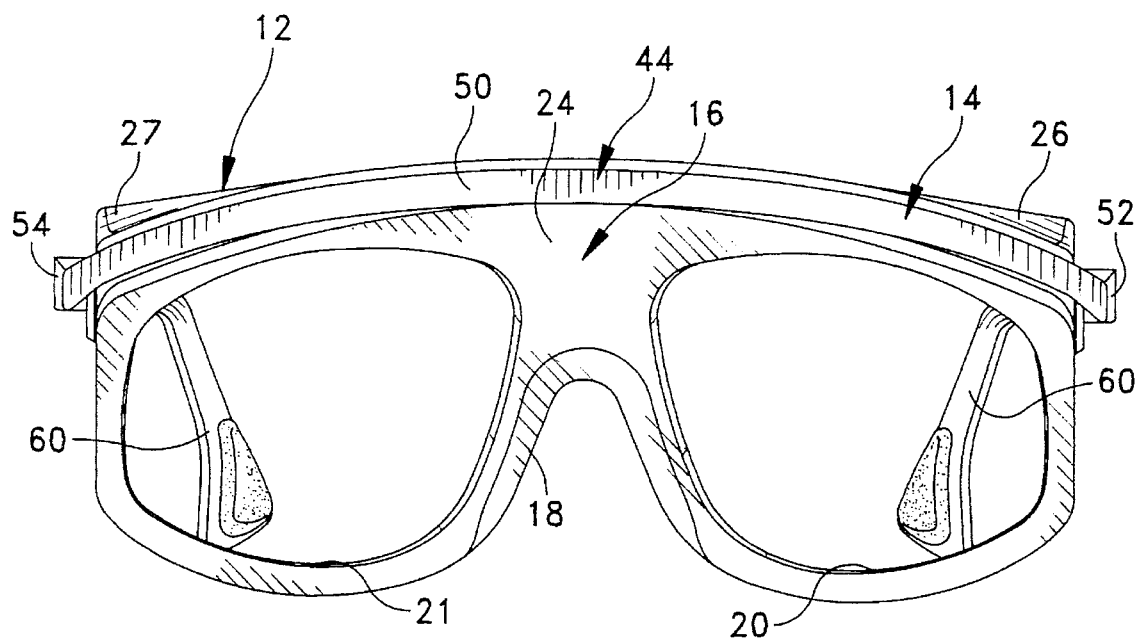
FIG. 4 is a front elevational view of the eyeglass assembly;.
Figure 5:
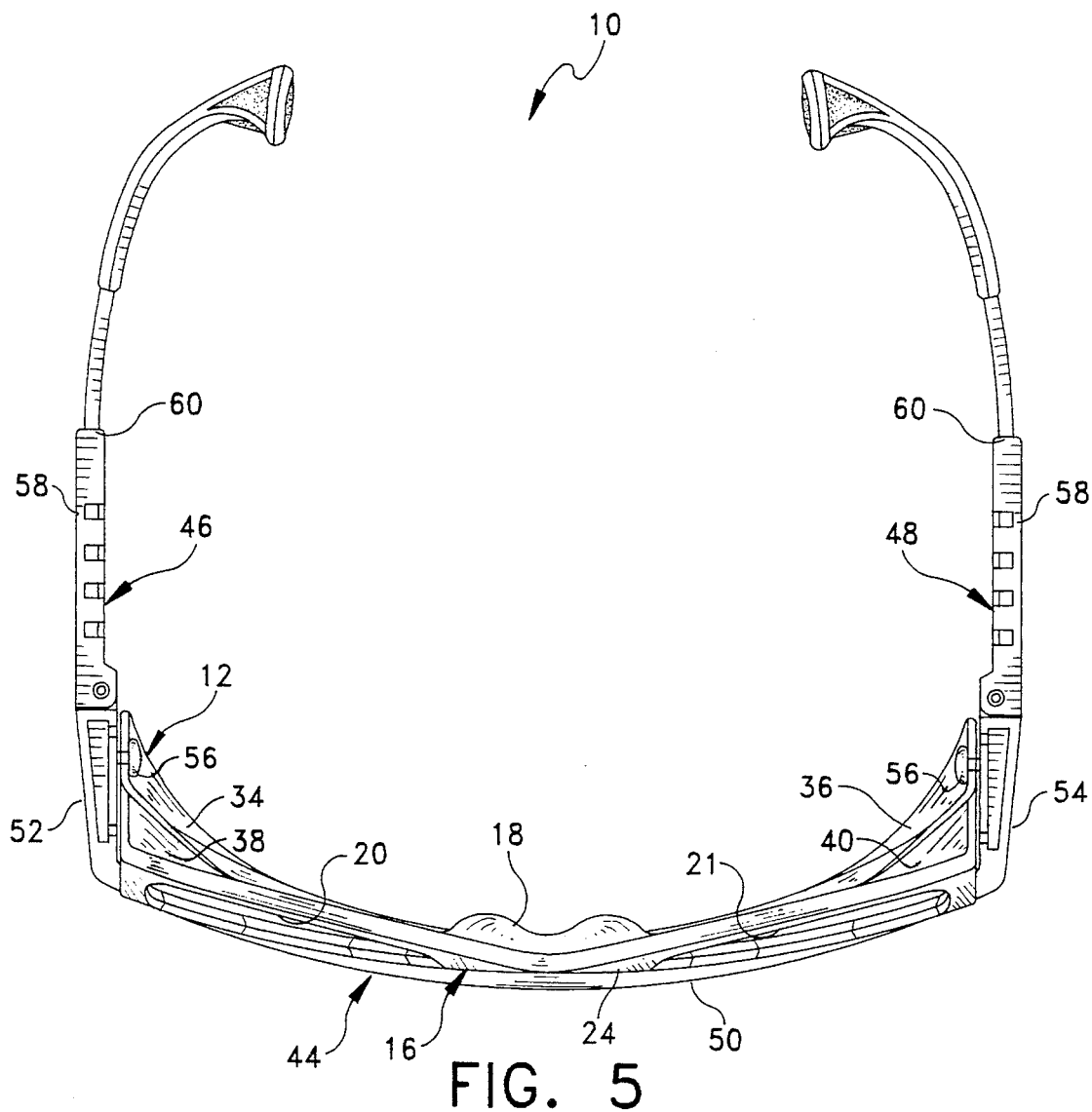
FIG. 5 is a bottom plan view thereof.
Figure 6:
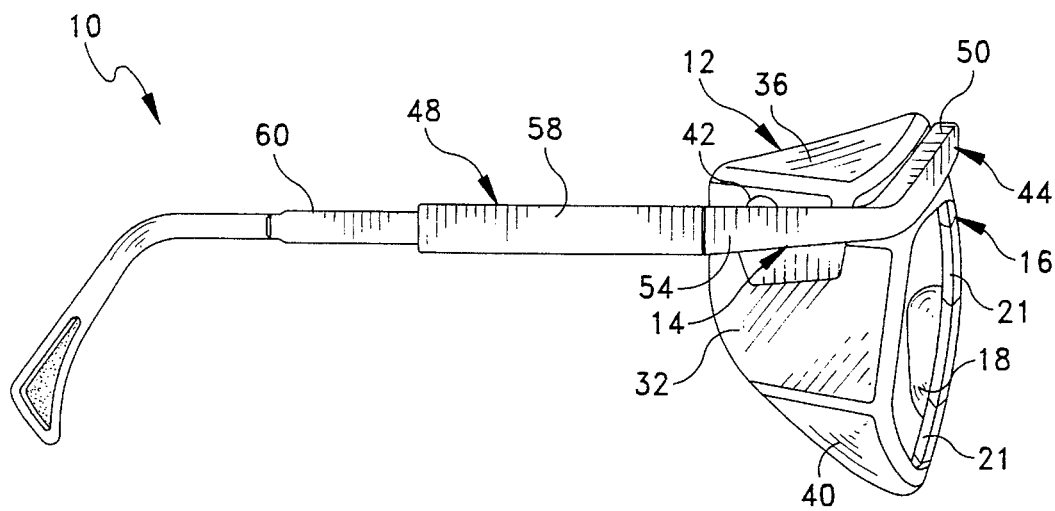
FIG. 6 is a side elevational view thereof.

Referring now to the drawings, the safety eyeglass assembly of the instant invention is illustrated and generally indicated at 10 in FIGS. 1, 2 and 4–6. The eyeglass assembly 10 comprises a carrier generally indicated at 12 which is adapted for receiving a pair of corrective lenses therein and a frame generally indicated at 14 which is removably and adjustably secured to the carrier 12 as will hereinafter be more fully set forth.

The carrier 12 is preferably integrally molded from a suitable, durable, transparent plastic material, and it includes a front panel portion generally indicated at 16 having a nose receiving portion 18 and left and right lens receiving apertures 20 and 21, respectively, formed therein. The nose receiving portion 18 is preferably formed with suitable nose pads for supporting the carrier 12 on the nose of a wearer, and the lens receiving apertures 20 and 21 are preferably adapted for snap receiving corrective lenses 22 and 23 therein. The front panel portion 16 is further preferably formed so that the lens receiving apertures 20 and 21 are formed in a main plate portion 24 thereof and so that the front panel portion also includes left and right rearwardly recessed upper portions 26 and 27 respectively, which are recessed rearwardly from the main plate portion 24 above the lens apertures 20 and 21, respectively. A reduced center aperture 28 is provided in the central upper portion of the front panel portion 16 for securing the carrier 12 to the frame 14 in a manner which will hereinafter be more fully set forth. The carrier 12 further comprises left and right side shields 30 and 32, respectively, which extend rearwardly from opposite side extremities of the front panel portion 16, left and right upper shields 34 and 36, respectively, which extend between the upper extremity portions of the front panel portion 16 and the left and right side shields 30 and 32, respectively, and left and right lower shields 38 and 40, respectively, which extend between the lower extremity portions of the front panel 16 and the left and right side shields 30 and 32, respectively. Each of the side shields 30 and 32 has an aperture 42 form therein for securing the carrier 12 to the frame 14 as will hereinafter be more fully set forth. In this regard, as will be noted, the apertures 42 are formed in vertically elongated irregular configurations to enable the angular position of the carrier 12 relative to the frame to be adjusted, as will also hereinafter be more fully set forth.

The frame 14 is of conventional construction, and it includes a front cross bar portion generally indicated at 44 and left and right temple portions generally indicated at 46 and 48, respectively. The front cross bar portion includes a front bar portion 50 and left and right side bar portions 52 and 54, respectively, and mushroom-shaped snap elements 56, which are integrally formed on the inner sides of the side bar portions 52 and 54 and are snap received in the apertures 42. As a result, the carrier 12 is adjustably securable in a plurality of different angular positions relative to the frame 14. The snap elements 56 include reduced shaft portions, as illustrated, which are engagable with the apertures 42 to adjustably position the side bar portions 52 and 54 at three different angular positions relative to the carrier 12. A reduced pin (not shown) is integrally molded on the inner side of the center portion of the front bar portion 50 and received in the reduced aperture 28 for further securing the frame 14 to the carrier 12 in a manner which allows pivoting of the front bar portion for adjusting the angular position of the frame 14 relative to the carrier 12. Each of the temple portions 46 includes a tubular front portion 58 and a rear portion 60 which is telescopically received in the front portion 58 thereof, and means (not shown) are provided on the portions of the rear portions 60 which are telescopically received in the front portions 58 for releasibly securing the rear portions 60 in various different telescopically adjusted positions relative to the front portions 58.

The frame 14 is adapted to be removably assembled with the carrier 12 in the manner illustrated. Specifically, the frame 14 is adapted to be assembled so that the snap elements 56 are releasibly received in the apertures 42 on the side shields 30 and 32 and so that the pin (not shown) on the rear side of the front bar portion 50 is received in the reduced aperture 28. When the frame 14 is assembled with the carrier 12 in this manner, the front bar portion 50 follows the contour of the rearwardly recessed portions 26 and 27 so that the front bar portion 50 has a somewhat greater degree of curvature than the front plate portion 24, and so that the opposite side portions of the front bar portion 50 are actually partially recessed rearwardly relative to the front plate portion 24. This allows the front plate portion 24 to be constructed in a somewhat flatter configuration to more effectively place the left and right lenses 22 and 23, respectively, in front of the eyes of a wearer. In any event, the frame 14 is angularly adjustable relative to the carrier 12 by repositioning the snap elements 56 in the apertures 42, and the temple portions 46 and 48 are longitudinally adjustable by telescopically repositioning the rear portions 60 in the front portions 58.

It is seen, therefore that the instant invention provides an effective safety eyeglass assembly which has significant advantages over the heretofore available safety eyeglasses. The carrier 12 is adapted for snap receiving a pair of corrective lenses therein, and it is integrally made from a transparent plastic material so that the carrier 12 with the lenses 22 and 23 provides a clear, unobstructed viewing assembly. Further, because the frame 14 is removably secured to the carrier 12, the frame 14 can be removed and replaced with another frame of a different color, or of a similar design but a different appearance. Accordingly, it is seen that the eyeglass assembly 10 and the carrier 12 represent significant advancements in the art relating to safety eyewear which have significant commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A safety eyeglass assembly comprising a lens carrier integrally molded from a transparent plastic material and including a front panel portion and left and right side shields extending rearwardly from left and right side extremities of said front panel portion, said front panel portion including a main front plate portion having a nose receiving portion and left and right lens receiving apertures adapted for snap receiving corrective lenses therein, said front panel portion further including left and right rearwardly recessed upper portions above said left and right lens apertures, said lens carrier further including left and right upper shields extending between left and right upper extremity portions of said recessed upper portions and said left and right side shields respectively, and left and right lower shields extending between left and right lower extremity portions of said main front plate portion and said left and right side shields respectively, said safety eyeglass assembly further comprising a frame detachably and adjustably secured to said carrier, said frame including left and right temple frame portions and a cross bar portion extending between said temple frame portions and passing in front of said front panel portion along said left and right recessed upper portions.

2. In the safety eyeglass assembly of claim 1, said left and right upper recessed portions having a first angle of curvature, said main front plate portion having an angle of curvature which is flatter than said first angle of curvature so that said corrective lenses are generally positioned in front of the user's eyes.

3. In the safety eyeglass assembly of claim 1, said cross bar portion being detachably secured to said carrier for detachably securing said frame thereto.

4. In the safety eyeglass assembly of claim 3, said cross bar portion including a front bar portion extending in front of said left and right recessed upper portions and further including left and right side bar portions extending along said left and right side shields, respectively.

5. In the safety eyeglass assembly of claim 4, said front bar portion, said right side bar portion and said left side bar portion being detachably secured to said carrier.

6. In the safety eyeglass assembly of claim 5, said front bar portion being detachably secured to said front panel portion at a center pivot point, said left and right side bar portions being detachably secured to said left and right side shields, respectively, such that said left and right side bar portions are vertically adjustable relative to said left and right side shields, respectively, for adjusting the angular orientation of said carrier relative to said frame.

7. In the safety eyeglass assembly of claim 1, said left and right temple frame portions being telescopically adjustable to different lengths.

8. A safety eyeglass assembly comprising a lens carrier integrally molded from a transparent plastic material and including a front panel portion and left and right side shields extending rearwardly from left and right side extremities of said front panel portion, said front panel portion including a main front plate portion having a nose receiving portion and left and right lens receiving apertures adapted for snap receiving corrective lenses therein, said front panel portion further including left and right rearwardly recessed upper portions above said left and right lens apertures, said safety eyeglass assembly further comprising a frame detachably and adjustably secured to said carrier, said frame including left and right temple frame portions and a cross bar portion extending between said temple frame portions and passing in front of said front panel portion along said left and right recessed upper portions.

9. In the safety eyeglass assembly of claim 8, said left and right upper recessed portions having a first angle of curvature, said main front plate portion having an angle of curvature which is flatter than said first angle of curvature so that said corrective lenses are generally positioned in front of the user's eyes.

10. In the safety eyeglass assembly of claim 8, said cross bar portion being detachably secured to said carrier for detachably securing said frame thereto.

11. In the safety eyeglass assembly of claim 8, said front bar portion, said right temple frame portion and said left temple frame portion being detachably secured to said carrier.

12. In the safety eyeglass assembly of claim 8, said left and right temple frame portions being telescopically adjustable to different lengths.

* * * * *